United States Patent [19]

Barton et al.

[11] Patent Number: 5,665,358
[45] Date of Patent: Sep. 9, 1997

[54] ANTIBODY DRUG-CONJUGATES

[75] Inventors: Russell L. Barton, Indianapolis; Deborah L. Guttman-Carlisle, Sheridan; Gary A. Koppel, Indianapolis, all of Ind.

[73] Assignee: Eli Lilly and Company, Indianapolis, Ind.

[21] Appl. No.: 649,568

[22] Filed: May 17, 1996

Related U.S. Application Data

[62] Division of Ser. No. 541,847, Oct. 10, 1995, which is a division of Ser. No. 40,323, Mar. 30, 1993, Pat. No. 5,556, 623.

[51] Int. Cl.$^6$ .......................... A61K 39/395; A61K 39/44
[52] U.S. Cl. ............................... 424/179.1; 424/181.1; 530/391.9; 536/6.4; 540/478
[58] Field of Search ..................... 424/179.1, 181.1; 530/391.9; 536/6.4; 540/478

[56] References Cited

U.S. PATENT DOCUMENTS

| | | | |
|---|---|---|---|
| 5,010,176 | 4/1991 | Barton | 530/388 |
| 5,028,697 | 7/1991 | Johnson et al. | 530/388 |
| 5,030,620 | 7/1991 | Hannart et al. | 514/18 |
| 5,045,451 | 9/1991 | Uhr et al. | 435/723 |
| 5,106,951 | 4/1992 | Morgan et al. | 530/391.9 |
| 5,122,368 | 6/1992 | Greenfield et al. | 530/327 |

OTHER PUBLICATIONS

Chemical Abstracts: vol. 68, 1968, abstract No. 87539e.
Borrebaeck, Journal of Immunological Methods, vol. 123, pp. 157–165 (1989).
Waldmann, Science, vol. 252, pp. 1657–1662 (1991).
Spalding, Bio/Technology, vol. 11, pp. 428–429 (1993).
Hermentin et al., Behring Inst. Mitt., No. 82, pp. 197–215 (1988).
Osband, et al., Immunology Today, vol. 11, No. 6, pp. 193–195 (1990).
Harris et al., TIBTECH, vol. 11, pp. 42–44 (1993).

*Primary Examiner*—Ponnathapura Achutamurthy
*Attorney, Agent, or Firm*—Paul J. Gaylo

[57] ABSTRACT

Immunoconjugates of antibodies or antigen-recognizing fragments of antibodies and monovalent cytotoxic drug derivatives make use of β-alanine derived linkers wherein the antibody or fragment thereof is attached to the linker's carboxy group via an ester or amide group and the drug is attached through the linker's 2-position methylene group. Intermediates, compositions and methods of use also are provided.

19 Claims, No Drawings

ANTIBODY DRUG-CONJUGATES

This application is a division of application Ser. No. 08/541,847 filed Oct. 10, 1995, which is a division of application Ser. No. 08/040,323 filed Mar. 30, 1993, U.S. Pat. No. 5,556,623.

FIELD OF THE INVENTION

The present invention belongs to the fields of organic chemistry, pharmaceutical chemistry, and immunology, and provides immunoconjugates which are vehicles for targeting large doses of pharmaceutically-active compounds to undesirable cells, tissues, and mammalian pathogens.

Immunoconjugates of the present invention consist of antibodies, preferably monoclonal antibodies which act as targeting agents, a pharmaceutically-active compound which has activity against the cell, tissue, or host in need of treatment, and an organic compound which joins or links ("linker") such antibodies with such pharmaceutically-active compounds. Intermediates for the preparation of the immunoconjugates are also provided.

BACKGROUND OF THE INVENTION

In recent years, pharmaceutical chemists have worked to provide more specific and potent drugs for the treatment of disease. In the case of cancer and other disease which function by the creation of specific abnormalities of cells, most of the useful drugs have been of the cytotoxic type which function by killing the abnormal cell. Such drugs are quite potent and may be hazardous to the recipient, even life-threatening.

In an attempt to direct a drug to particular cells, tissues, or pathogen within a host, efforts have been made to develop a mechanism for targeting such drugs, particularly highly cytotoxic drugs, directly to the afflicted area or pathogen, without administering a whole-body dosage. However, no antibody-drug conjugate has been approved for therapeutic use. The present invention expands the scope of immunoconjugate technology by providing novel immunoconjugates useful for cell-/tissue-/pathogen-specific drug delivery in mammals and intermediates thereto.

SUMMARY OF THE INVENTION

The present invention provides a physiologically-acceptable drug conjugate of formula I

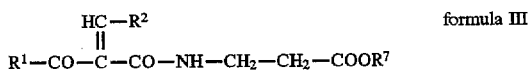

wherein $R^1$ is $C_1$–$C_4$ alkyl;

$R^2$ is a monovalent drug derivative having a reactively-available amino, hydroxy or thiol function;

m is an integer from 1 to 10; and

Ab is an antibody, or antigen-recognizing fragment thereof, which recognizes an antigen associated with a cell, tissue, or pathogen to which delivery of the drug is desirable.

The invention also provides intermediates of the following formulae

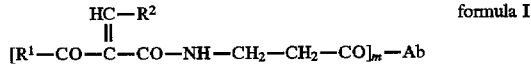

wherein $R^1$ is $C_1$–$C_4$ alkyl;

$R^4$ is a carboxy protecting group;

$R^5$ is $H_2$, $=C(OH)_2$, $=CHOR^6$, or $=CHSR^6$; and $R^6$ is $C_1$–$C_4$ alkyl; and

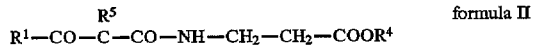

formula III wherein $R^1$ is $C_1$–$C_4$ alkyl;

$R^2$ is a monovalent drug derivative having a reactively-available amino, hydroxy or thiol function; and $R^7$ is H, a carboxy protecting group, or a carboxy activating group, or a moiety which completes a salt of the carboxy group.

The present invention further provides pharmaceutical compositions comprising an immunoconjugate of the invention and a parenterally-administrable medium. Also provided are treatment methods comprising the parenteral administration of an immunoconjugate of the invention to a patient in need of treatment with a pharmaceutically active compound (drug).

DETAILED DESCRIPTION OF THE INVENTION

The present invention pertains to novel immunoconjugates, intermediates thereto, pharmaceutical compositions and methods of use.

Throughout the present document, all temperatures are in degrees celsius. All expressions of percentage, concentration and the like are in weight units, unless otherwise stated. All references to concentrations and dosages of drug conjugates are in terms of the amount or concentration of the drug contained in the conjugate.

In the above formulae, the general and specific chemical terms used have their normal meanings in organic and, especially, amino acid chemistry.

For example, the term "$C_1$–$C_4$ alkyl" refers to straight or branched aliphatic chains of 1–4 carbon atoms including methyl, ethyl, propyl, isopropyl, n-butyl, isobutyl, sec-butyl and tert-butyl.

The carboxy protecting groups of $R^4$ and $R^7$, when $R^7$ is neither H nor an activating group, denote groups which generally are not found in final therapeutic conjugates, but which are intentionally introduced during a portion of the synthetic process to protect a group which otherwise might react in the course of chemical manipulations, and is then removed at a later stage of the synthesis. Since compounds bearing such protecting groups are of importance primarily as chemical intermediates, their precise structure is not critical. Numerous reactions are described in a number of standard works including for example, Protective Groups in Organic Chemistry, Plenum Press, (London and New York, 1973); Green, T. W., et al. (eds), Protective Groups in Organic Synthesis, Wiley (New York, 1981); and Schroeder, et al. (eds.), The Peptides, Vol. I, Academic Press (London and New York, 1965).

Preferred $R^4$ and $R^7$ carboxy protecting groups include $C_1$–$C_4$ alkyl, phenyl which maybe substituted, and benzyl which may be substituted. The term "phenyl which may be substituted" denotes an unsubstituted or substituted phenyl residue, optionally having one or two substituents selected from halo (bromo, chloro, fluoro, and iodo), nitro, $C_1$–$C_4$ alkyl and $C_1$–$C_4$ alkoxy. The term "benzyl which may be substituted" denotes an unsubstituted or substituted benzyl ring, optionally having one or two substituents selected from halo, nitro, $C_1$–$C_4$ alkyl and $C_1$–$C_4$ alkoxy. The term "$C_1$–$C_4$ alkoxy" represents a $C_1$–$C_4$ alkyl group attached through an oxygen bridge such as, for example, methoxy, ethoxy, n-propoxy, isopropoxy, and the like. Unsubstituted and substituted benzyl are especially preferred carboxy protecting groups.

The term "carboxy activating group" refers to groups used in synthetic organic chemistry which increase the reactivity of a carboxy group. Such groups are well known in the organic synthetic art and, when bound with the single-bonded oxygen of a carboxy group, include groups such as, for example, benzenesulfonyloxy, methanesulfonyloxy, toluenesulfonyloxy, phthalimidyloxy, succinimidyloxy, chloro, benzotriazolyloxy, bromo, azido, and the like. Preferred carboxy activation groups include benzotriazolyloxy and phthalimidyloxy while succinimidyloxy is especially preferred.

The immunoconjugates of the present invention are composed of antibodies, drugs of certain chemical classes, and organic chemical groups which link the antibodies and drugs. The invention also provides β-alanine derivative intermediates which are useful for the preparation of such immunoconjugates.

The Antibody

It will be understood that the function of the present drug conjugates is determined by the biological efficacy of the drug and the antigenic selectivity of the antibody. An antibody is chosen which will recognize an antigen associated with a cell, tissue or pathogen to which the particular drug is delivered to the benefit of a patient. For example, if the drug is an antineoplastic, then an antibody which recognizes an antigen associated with tumor cells would be chosen.

In addition to antineoplastic agents, other antiproliferative agents such as those used in the treatment of cardiovascular disease may be selected to be "linked" with site-specific antibodies. For example, it is well established that restinosis frequently follows angioplasty. The site-specific delivery of antiproliferative drugs to areas where atheriosclerotic plaque was removed would be useful in retarding or preventing reocclusion.

Likewise, an antibacterial or antiviral drug would be linked to an antibody which would recognize a respective bacterium or virus.

Depending upon the characteristics of the drug to be used, it may be preferred in a given case to choose an antibody which is internalized by the cell, or it may be preferred to use an antibody or antigen-binding fragment thereof which remains on the cell surface by recognizing a surface antigen.

The source of the antibody is not critical to the present invention. It may be chosen from any class or subclass of immunoglobulin including IgG, IgA, IgM, IgE and IgD. Similarly, the species of origin is not critical so long as the antibody targets a cell where the effect of the drug is useful.

In the present state of the art, monoclonal antibodies and their fragments are frequently used in drug conjugates, and use of them is preferred in the present invention. However, polyclonal antibodies and their fragments are not excluded.

Newer types of antigen binding molecules can be produced by recombinant technology. See, e.g., Hodgson, *Bio/Technology*, 9: 421–25 (1991). More specifically, genetically engineered antibodies which retain the epitope specificity of monoclonal antibodies are now known in the art and provide a less immunogenic molecule. Such genetically engineered antibodies are also embraced by the present invention.

Furthermore, chimeric antibodies are described in U.S. Pat. No. 4,816,567 (Cabilly), which is herein incorporated by reference.

A further approach to production of genetically engineered antibodies is provided in U.S. Pat. No. 4,816,397 (Boss) which is also herein incorporated by reference. The approach of U.S. Pat. No. 4,816,397 has been further refined as taught in European Patent Publication 0 239 400 which published Sep. 30, 1987. The teachings of European Patent Publication 0 239 400 (Winter) are the preferred format for the genetic engineering of monoclonal antibodies which are used as components of the immunoconjugates of the invention. The Winter technology involves the replacement of complementary determining regions (CDRs) of a human antibody with the CDRs of a murine monoclonal antibody, thereby converting the specificity of the human antibody to the specificity of the murine antibody which was the source of the CDR regions. The CDR technology provides a molecule which contains minimal murine sequences and, thus, is less immunogenic.

Single chain antibody technology is yet another variety of genetically engineered antibody which is well known in the art. See, Bird, R. E., et al., *Science*, 242: 423–426 (1988). The single chain antibody technology involves joining the binding regions of heavy and light chains with a polypeptide sequence to generate a single polypeptide having the binding specificity of the antibody from which it was derived.

The aforementioned genetic engineering approaches provide the skilled artisan with numerous means to generate molecules which retain the binding characteristics of the parental antibody while affording a less immunogenic format. Thus, genetically engineered antibodies may be obtained and used in the present invention.

The origin and nature of the antibody is not otherwise critical, so long as it targets the cell, tissue or pathogen to be treated and is not, in itself, toxic to the patient. Some discussion of the method of evaluating antibodies and conjugates will be provided for convenience.

First, the antibody should be produced by a hybridoma or modified microorganism which is sufficiently stable to allow preparation of reasonable quantities of antibody. The antibody itself should be amenable to purification and, in particular, should be sufficiently water-soluble to allow chemical manipulations at reasonable concentrations.

Next, conjugates prepared with the candidate antibody are evaluated for antigen-binding capacity. Skilled artisans will appreciate the ease with which any diminution in antigen binding activity can be determined. Competitive radioimmunoassays (RIAs) and flow cytometry are two of the most convenient means for determining whether a conjugate has reduced binding capacity relative to the pristine antibody. A modest reduction from the binding capacity of the free antibody is expected and acceptable. Then, the conjugate is tested to determine its in vitro potency, such as cytotoxicity in the case of anticancer drugs, against antigen-positive cells. An effective conjugate can have potency somewhat less than the free drug in the same assay because of its ability to bring a high concentration of drug to the cell. A conjugate which is accepted in the first two tests is then evaluated in a nude mouse human tumor xenograft model as taught by Johnson and Laguzza, *Cancer Res.*, 47: 3118–22 (1987). The candidate conjugate should be tested, for example, in nude mice against the free drug, a mixture of free drug and free antibody, and a conjugate with a non-targeting immunoglobulin. The conjugate should generally exhibit improved potency or safety. Dose ranging studies should be carried out in the xenograft model.

Conjugates which are potent in the xenograft model are submitted to tests in animals which are known to express the antigen of interest in a pattern similar to that seen in humans.

If the conjugate produces a significant degree of binding to the antigen in such tests, and if it is reasonably free of toxicity at doses predicted by the xenograft model to be therapeutic, the candidate conjugate can be considered to have therapeutic potential.

It will be understood that properly chosen fragments of antibodies have the same effect as the intact antibody. Skilled artisans will recognize the utility which the proteolytic enzymes papain and pepsin possess for cleaving immunoglobins into fragments which are bivalent or monovalent, respectively. Thus, in the practice of this invention, fragments of antibodies, particularly $F(ab')_2$ fragments, which recognize an antigen associated with the cell to be treated, may be just as useful as are intact antibodies. Fab fragments are also useful.

The mechanism by which the linker group reacts and attaches to the antibody depends on the $R^7$ group in the linker of formula III wherein $R^7$ is a carboxy activating group. The linking mechanism of the $R^7$ group will be explained below in detail in the section on synthesis of the conjugates.

Formula I indicates that from 1 to 10 linker-drug moieties (derivatized drug) are attached to each molecule of antibody. Of course, the number of such moieties per antibody molecule is an average number because a given batch of conjugate will necessarily contain molecules having a range of ratios of derivatized drug to antibody. The most efficient use of the expensive antibody is obtained, of course, when a number of molecules of drug are attached to each antibody molecule. However, the attachment of an excessive number of molecules of derivatized drug usually has an adverse effect on the antibody's ability to recognize and bind to its antigen, so a compromise value for m must be found.

Generally, the preferred average value for m is from 3 to 6. Conjugation ratios are easily determined by measuring the absorbance of the immunoconjugate at wave-lengths selected to detect the drug, the linker, peptide bonds, et cetera, and then deduce from the absorbance data and the extinction coefficients for the various components the average amount of drug per antibody.

A great number of antibodies are available to immunologists for use in the present invention, and further useful antibodies are being disclosed in every issue of the relevant journals. It is impossible, and entirely unnecessary, to give an exhaustive listing of antibodies which can be applied in the practice of this invention. Immunologists and chemists of ordinary skill are entirely able to choose antibodies from sources such as the catalogue of the American Type Culture Collection (ATCC), Rockville, Md., U.S.A., and *Linscott's Directory of Immunological and Biological Reagents*, published by Linscott's Directory, 40 Glen Drive, Mill Valley, Calif., U.S.A., 94941. Thus, it is a simple matter for the artisan in the field to choose an antibody against virtually any determinant, such as tumor, bacterial, fungal, viral, parasitic, mycoplasmal, or histocompatibility antigens, as well as pathogen surface antigens, toxins, enzymes, allergens and other types of antigens related to physiologically important cells and tissues.

The most preferred use of the present invention is in the delivery of cytotoxic drugs to cancer cells, particularly including squamous carcinoma cells, adenocarcinoma cells, small cell carcinoma cells, glyoma cells, melanoma cells, renal cell carcinoma cells, transitional cell carcinoma cells, sarcoma cells, cells of supporting tumor vasculature, and cells of lymphoid tumors such as leukemias and lymphomas. Appropriate antibodies for the targeting of all such cells are available, and sources can be located in Linscott.

Alternatively, the necessary hybridomas for the production of such antibodies by conventional methods are obtainable through the ATCC and other cell line collections.

A number of presently known antibodies are particularly interesting for use in the anticancer aspect of the present invention. Preferred specific antibodies, for example, are VX007B, $CC_{83}$, $CC_{49}$ and D612.

Another interesting antibody is KS1/4, first disclosed by Varki, et al., *Cancer Research*, 44:681–86 (1984). A number of plasmids which comprise the coding sequences of the different regions of monoclonal antibody KS1/4 are now on deposit and can be obtained from the ATCC, Peoria, Ill., U.S.A. The plasmids can be used by those of ordinary skill to produce chimeric antibodies by recombinant means, which antibodies bind to a cell surface antigen found in high density on adenocarcinoma cells. The construction of such antibodies is discussed in detail in U.S. Pat. No. 4,975,369. The following plasmids relate to KS1/4.

Plasmid $pGKC_{2310}$, the coding sequence of the light chain, the signal peptide associated with the light chain, and the 5' and 3' untranslated regions; isolated from *E. coli* K12 MM294/$pGKC_{2310}$, NRRL B-18356.

Plasmid pG2A52, the coding sequence of the heavy chain, the coding sequence of the signal peptide associated B with the heavy chain, and the 5' and 3' untranslated regions; isolated from *E. coli* K12 MM294/pG2A52, NRRL B-18357.

Plasmid $CHKC_2$-6, the coding sequence of the light chain variable region, the coding sequence of the signal peptide associated with the light chain, and a sequence encoding the light chain constant region of human IgG; isolated from *E. coli* K12 DH5/$CHKC_2$-6, NRRL B-18358.

Plasmid $CHKC_2$-18, the coding sequence of a derivative light chain variable region, the coding sequence of the signal peptide associated with the light chain, and a sequence encoding the light chain constant region of a human IgG; isolated from *E. coli* K12 DH5/$CHKC_2$-18, NRRL B-18359.

Plasmid CH2A5, the coding sequence of the heavy chain variable region, the coding sequence of the signal peptide associated with the heavy chain, and a sequence encoding the heavy chain constant region of human IgG1; isolated from *E. coli* K12 MM294/CH2A5, NRRL B-18360.

Plasmid CH2A5IG2, the coding sequence of the heavy chain variable region, the coding sequence of the signal peptide associated with the heavy chain, and a sequence which encodes the heavy chain constant region of human IgG2; isolated from *E. coli* K12 DH5/CH2A5IG2, NRRL B-18361.

Plasmid CH2A5IG3, the coding sequence of the heavy chain variable region, the coding sequence of the signal peptide associated with the heavy chain, and a sequence encoding the heavy chain constant region of human IgG3; isolated from *E. coli* K12 DH5/CH2A5IG3, NRRL B-18362.

Plasmid CH2A5IG4, the coding sequence of the heavy chain variable region, the coding sequence of the signal peptide associated with the heavy chain, and a sequence encoding the heavy chain constant region of human IgG4; isolated from *E. coli* K12 DH5/CH2AIG4, NRRL B-18363.

Antibody 5E9C11, produced by an ATCC hybridoma, HB21, recognizes the transferrin receptor which is expressed by many tumors. An antibody named B72.3, available from the National Cancer Institute, recognizes antigens expressed by both breast and colon carcinoma.

Two interesting antibodies with reactivities against non-tumor antigens are OKT3 and OKT4. These antigens bind to peripheral T-cells and human T-helper cells, respectively.

Additional sources of antibodies useful for various therapeutic purposes include, for example, the following. Anti-human lymphocyte and monocyte antibodies, useful for immune modulation and tumor therapy, are produced by ATCC cultures, HB2, HB44, HB78 and HB136. An anti-transferrin receptor antibody, useful for tumor therapy, is produced by ATCC culture HB84. ATCC culture HB8059 produces an antibody against colorectal carcinoma monosialoganglioside, and culture B8136 produces an antibody against mature human T-cell surface antigen, useful for immune modulation and T-cell leukemia therapy.

Furthermore, ATCC hybridoma HB9620 will produce a convenient anticarcinoembryonic antigen called CEM231.6.7.

Schlom, et al. have disclosed a number of interesting antibodies which have affinities for tumor-related antigens. In particular, the following articles and patents by that group are important.

*Cancer Research*, 50: 1291–98 (1990)

*Cancer Research*, 45: 5769–80 (1985)

*International J. Cancer*, 43: 598–607 (1989)

U.S. Pat. No. 4,522,918

U.S. Pat. No. 4,612,282

European Patent Publication 0,394,277

European Patent Publication 0,225,709

The antibodies taught by the Schlom group which are functional in the context of the present invention include those with the designations D612, COL-1 through COL-15, CC-1, CC-8, CC-9, CC-11, CC-14, CC-15, CC-20, CC-26, CC-29, CC-30, CC-41, CC-46, CC-48, CC-49, CC-52, CC-55, CC-57, CC-60, CC-63, CC-66, CC-72, CC-74, CC-78, CC-83, CC-87, CC-90, CC-92.

An immunologist or one knowledgeable in the art of drug targeting, with the assistance of the commonly known publications in the field and the above guiding examples and description, can readily choose an antibody for the targeting of any appropriate drug to any desired cell to be treated with that drug.

Methods of producing and purifying monoclonal antibodies are also well known to one skilled in the art of immunology. For a review of methods for culturing hybridomas, generating ascites, and purifying antibodies, see, Mishell, B., et al. (eds), *Select Methods in Cellular Immunology*, W. H. Freeman and Company (New York, 1980).

The Drug

It will be understood that the essence of the present invention is the method of linking a monovalent drug derivative (hereinafter drug) and antibody by means of the above-described β-alanine derived linkers, and that neither the drug nor the antibody is a limitation of the present invention. The linkers of the present invention, accordingly, may be and are beneficially used when applied to drugs of any therapeutic or prophylactic purpose, limited only by the necessity for the drug to possess a chemical function with which the β-alanine derivative can link, and the necessity for the antibody to target a cell where the drug is beneficial. The methylidene linking mechanism provided by the present invention requires the drug to have a reactively-available amino, hydroxy or thiol function. Furthermore, the drug must be of such a nature that the reaction of the reactively-available function with the linker does not destroy the activity of the drug.

Accordingly, the present linker invention may be used in connection with drugs of substantially all classes including, for example, antibacterials, antivirals, antifungals, anticancer agents, antimycoplasmals, and the like. The drug conjugates so constructed are effective for the purpose for which the corresponding drugs are effective, and have superior efficacy because of the ability, inherent in the antibody, to transport the drug to the cell, tissue or pathogen which would respond to such drug therapy.

Drugs and other compounds which may be subjected to drug conjugation are disclosed in U.S. Pat. Nos. 5,010,176 and 4,671,958, and the disclosure concerning drugs of these patents is herein incorporated by reference.

As previously stated, the drug is reacted with the linker through a reactively-available amino, hydroxy or thiol function on the drug. The reactively-available functionality of the drug may originally be part of the drug or may be introduced for the purpose of forming a derivatized drug. The term "reactively-available amino function" includes amino groups which are part of hydrazides, hydrazines, carbamates, and the like, as well as amino groups simply attached to a carbon-hydrogen structure. An amino group may have a third small substituent on it providing the group does not create steric hindrance which prevents reaction with the β-alanine derivative structure. Such groups may be, for example, straight- or branched-chain alkyl groups and the like.

Similarly, the terms "reactively-available hydroxy function" and "reactively-available thiol function" include simple alcohols and carboxylic acid, and thioic acid, respectively.

While the use of drugs of any chemical type having a reactively-available function and any therapeutic or prophylactic efficacy is included in the present invention, it is preferred to use drugs which have an amino function available for reaction. It is more preferred to use drugs wherein the amino group is part of a hydrazine or hydrazide moiety.

The most preferred efficacy class of drugs for use in the present invention is the class of cytotoxic drugs and, particularly, those which are used for cancer therapy. Such drugs include, in general, alkylating agents, antiproliferative agents, tubulin binding agents, and the like.

Preferred classes of cytotoxic agents include, for example, the daunomycin family of drugs, the vinca drugs, the mitomycins, the bleomycins, the cytotoxic nucleosides, the pteridine family of drugs, and the podophyllotoxins.

Particularly useful members of those classes include doxorubicin, daunorubicin, aminopterin, methotrexate, lometrexol, methopterin, dichloromethotrexate, mitomycin C, porfiromycin, 5-fluorouracil, 6-mercaptopurine, cytosine arabinoside, podophyllotoxin, etoposide, melphalan, vinblastine, vincristine, leurosidine, vindesine, leurosine, or derivatives thereof, and the like. Of these, vinblastine and derivatives thereof, particularly desacetylvinblastine and derivatives thereof, and doxorubicin and derivatives thereof are especially preferred drugs. Desacetylvinblastine hydrazide and doxorubicin are hereinafter characterized as DAVLB-NHNH$_2$ and DOX-NH$_2$, respectively.

It will be understood that chemical modifications may be made by the ordinarily skilled artisan to the preferred and generally described compounds in order to make reactions of them more convenient.

It will also be understood that preferred immunoconjugates are prepared from the preferred drugs.

The Intermediates

The intermediate β-alanine derivatives of the present invention (formulas II and III) are the intermediates which are reacted with the antibody and the drug and, thus, are the precursors of the linker which joins the antibody and the drug. Accordingly, the preferred β-alanine derivative intermediates confer their structure on the preferred immunoconjugates of the present invention.

The intermediates are derived of β-alanine and are prepared according to processes known or readily imagined by ordinarily skilled organic chemists.

Synthesis of the Intermediate Beta-alanine Derivatives

The intermediate β-alanine derivatives of the present invention are prepared by processes known to one skilled in the organic chemical art using readily available reagents.

In the first step to prepare the novel intermediates of the present invention, a protected β-alanine compound of formula IV is reacted with a diketene of formula V in an inert solvent or mixture of solvents in the presence of a base such as N-methylmorpholine and the like. One will recognize that the length of the $R^8$ substituent of formula V ($C_1$–$C_3$ alkyl) dictates the length of the $R^1$ substituent in compounds of formula I, II, and III. This reaction, which produces compounds of formula IIa, is known in the art and is depicted below in Equation 1.

Equation 1

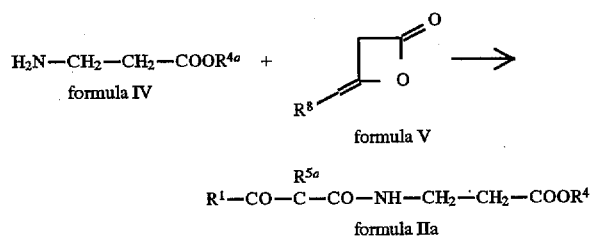

formula IIa wherein $R^1$ is $C_1$–$C_4$ alkyl;

$R^{4a}$ is a carboxyl protecting group;

$R^{5a}$ is $H_2$; and $R^8$ is H or $C_1$–$C_3$ alkyl.

Suitable solvents are any polar solvent, or mixture of solvents, which will remain inert or substantially inert under reaction conditions. Preferably, a mixture of solvents containing methylene chloride and dimethylformamide (DMF) is used in this reaction. A preferred ratio of these preferred solvents is 5:1, respectively.

The amount of reactants and reagents, the temperature employed, and the length of time that is required to effect this reaction is known in the art and is apparent to a skilled organic chemist (see, e.g., Example 1).

The second step in synthesizing the compounds of the present invention preferably requires reacting a compound of formula IIa with an appropriate trialkylorthoformate such as triethylorthoformate and the like, in the presence of a Lewis acid such as zinc chloride and the like, and an alcohol scavenger such as acetic anhydride and the like, to form an alkoxymethylidene derivative of formula IIb. This reaction is carried out at an elevated temperature, in the range of 100°–200°, and is completed in a few hours time. Equation 2 below depicts this preferred reaction. Alternatively, $R^5$ may be alkylthiomethylidene by using procedures well known in the art.

Equation 2

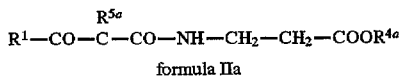

formula IIa wherein

-continued
Equation 2

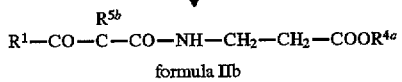

$R^1$—CO—C—CO—NH—CH$_2$—CH$_2$—COOR$^{4a}$
formula IIb wherein $R^1$ and $R^{4a}$ are as defined above; and $R^{5b}$ is =C(OH)$_2$, =CHOR$^6$, or =CHSR$^6$; or $R^6$ is $C_1$–$C_4$ alkyl.

In each reaction of the present invention, no unusual excess amount of starting compounds is necessary. As is ordinarily the case in organic chemistry, it is advisable to use a moderate excess of comparatively inexpensive reactants in order to assure that more expensive reactants are fully consumed. This rule is particularly true in the case of the reactions with antibodies which typically are expensive and difficult to prepare and purify. In general, however, amounts of excess reactants may be utilized for the purpose of maximizing the economy of the process, bearing in mind the cost of the ingredients as well as throughput of the equipment. Thus, it is unnecessary to use excess amounts of reactants merely to force the reactions to occur.

In the third step of the process used to prepare intermediates of the present invention, formula IIb compounds are catalytically hydrogenated, in the presence of a suitable solvent, to form compounds of formula IIc. In this well known reaction, the purpose of which is to remove the $R^{4a}$ carboxyl protecting group and form the acid thereof, 1,4-cyclohexadiene is the preferred reducing agent.

Suitable hydrogenation catalysts include noble metals and oxides such as palladium, platinum and rhodium oxide on a support such as carbon or calcium oxide. However, palladium-on-carbon is preferred.

Solvents for this reaction are those solvents or mixture of solvents which remain inert throughout the reaction. Typically, alcohols such as methanol, 1-propanol, 2-propanol and, especially, ethanol, are suitable solvents.

In addition to the free acid, the $R^{4a}$ carboxylic acid may be further derivatized to its salt form. The salts are formed with any moiety capable of forming a physiologically-acceptable salt of the carboxylic acid. Alkali metal and hydrohalide salts are particularly appropriate. Thus, the sodium, potassium and lithium salts, as well as the hydrochloride, hydrobromide and hydrofluoride salts, are particularly useful in the practice of the present invention. Other salts acceptable in pharmaceutical chemistry, however, are also useful. For example, amine salts such as triethylamine, triethanolamine, ethyldimethylamine and the like are useful, as are quaternary ammonium salts including tetraalkylammonium salts, (benzyl or phenyl) trialkylammonium salts and the like. Among ammonium salts, tetrabutylammonium, benzyltrimethylammonium, and tetramethylammonium are typical and preferred salts. Pharmaceutical chemists frequently use salts of carboxylic acids and the present salts, wherein $R^{4b}$ is a salt-forming moiety, may be prepared with any base which forms a physiologically-acceptable salt.

This aspect of the process is depicted in Equation 3.

Equation 3

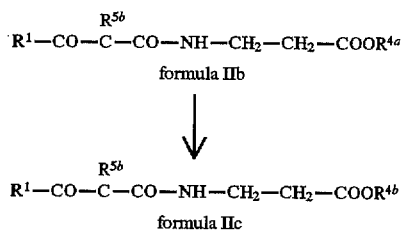

$R^1$ and $R^6$ are as defined above;
$R^{5b}$ is $=C(OH)_2$, $=CHOR^6$, or $=CHSR^6$; and
$R^4$ is H or a moiety which completes a salt of the carboxylic acid.

Especially preferred substituents for formula II compounds is as follows:

| COMPOUND | SUBSTITUENT | | |
|---|---|---|---|
| | $R^1$ | $R^4$ | $R^5$ |
| IIA | methyl | benzyl | $—H_2$ |
| IIb | methyl | benzyl | ethyloxymethylidene |
| IIc | methyl | H | ethyloxymethylidene |

Compounds of formulae IIa, IIb, and IIc are each novel, are useful for the preparation of immunoconjugates of the present invention, and are collectively incorporated into compounds of formula II herein.

Reactions with Intermediates and Drugs

The intermediates of formula IIc are reacted with drugs under conditions which will allow the alkylthiol, alcohol or alkoxy group of the $R^{5b}$ substituent to be cleaved, and the remaining methylidenyl group to react with the reactively-available amino, hydroxy or thiol function of the drug. In general, the reactions are carried out at temperatures from about $-30°$ to about $50°$, in inert organic solvents or in aqueous mixtures of such organic solvents, and usually in the presence of mild bases such as alkali metal bicarbonates, carbonates and hydroxides. Generally, the reactions are quantitative and require no unusual excess amounts of reactants. This reaction provides the derivatized drug compounds of formula IIIa

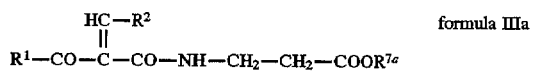

wherein
$R^1$ is $C_1$–$C_4$ alkyl;
$R^2$ is a monovalent drug derivative having a reactively-available amino, hydroxy or thiol function; and
$R^{7a}$ is H or a moiety which completes a salt of the carboxylic acid or, in the alternative, a carboxy protecting group which will later be reduced to form the acid or a moiety which completes a salt of the carboxylic acid.

Isolation of the product may require chromatography under high pressure or other sophisticated procedures because it usually is important to purify the derivatized drug with considerable care. Because the derivatized drug is later reacted with the antibody to complete preparation of the immunoconjugate, any reactive impurity which accompanies the derivatized drug may consume reactive sites on the antibody.

The removal of the carboxy protecting group from a formula IIb compound, in Equation 3, may be accomplished either before or after the β-alanine derivative intermediate is reacted with the drug. If it is necessary to use protecting groups on the drug, it may well be possible for those groups to be removed under the same conditions which remove the above-mentioned protecting group. Thus, the drug may first be reacted with a compound of formula IIb and both the drug and the β-alanine derived intermediate are deprotected, or a formula IIb compound is first deprotected and a formula IIc compound is reacted with the drug, forming a compound of formula IIIa.

Carboxy Activating Groups

In preparation for reacting the derivatized drug with the desired antibody, the carboxylic acid or salt moiety of formula IIIa is first activated. The process of activating a carboxylic acid (where $R^{7a}$ of formula IIIa compounds is H or a salt moiety thereof) is well known in the art and is generally accomplished by use of conventional esterification reagents such as carbodiimides, particularly dicyclohexylcarbodiimide, and an activating group such as N-hydroxysuccinimide and the like. Compounds of formula IIIb result from this reaction

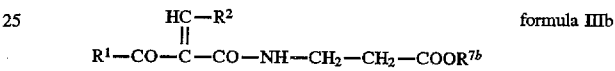

wherein
$R^1$ and $R^2$ are as described above; and
$R^{7b}$ is a carboxy activating group.

Especially preferred $R^1$ and $R^7$ groups for formula IIIa compounds are methyl and hydrogen, respectively; especially preferred $R^1$ and $R^{7b}$ substituents for formula IIIb compounds are methyl and N-hydroxysuccinimide, respectively.

Reactions with activating groups are carried out in an inert organic solvent such as, for example, dioxane, tetrahydrofuran, chlorinated hydrocarbons, and the like or a mixture thereof. These reactions generally may be performed at moderate temperatures in the range from about $0°$ to about $50°$.

Compounds of formula IIIa and IIIb are each novel, are useful for the preparation of immunoconjugates of the present invention, and are collectively incorporated into compounds of formula III herein.

Synthesis of the Immunoconjugates

Once a derivatized drug is made, as is described above (formula III), it is reacted with the antibody as the final step in preparing the conjugate.

The primary concern in choosing the conditions under which to react the derivatized drug with the antibody is maintaining the stability of the antibody. The reaction must be carried out in an aqueous medium of a composition which will not harm the antibody. A particularly suitable aqueous medium is a sodium carbonate buffer solution, in which the concentration of carbonate ion is in the range of about 0.05 to about 0.5 molar. The reaction also may be carried out in slightly acidic phosphate buffers, and physiological phosphate buffered saline (ppbs) and the like. Although the reaction medium should be aqueous, small amounts of organic solvents in the reaction medium are not harmful providing the solvents do not have a tendency to damage the antibody.

The pH of the reaction medium should be maintained at a range from about 7 to about 9, and reaction of the derivatized drug with the antibody must be carried out at temperatures from about $4°$ to about $40°$.

Because the solubility of antibodies is not great, the concentration of the antibodies in the reaction medium should be maintained at relatively low concentrations. For example, the concentration of antibody is usually in the range of from about 5 to about 25 mg per mL of aqueous medium.

As described above, from about 1 to 10 moles of derivatized drug are attached to each mole of antibody. In order to obtain this conjugation ratio, it is usually necessary to use an excess quantity of a formula III derivatized drug. The reactivity of antibodies and active esters is somewhat variable but, in general, from about 5 to about 15 moles of derivatized drug per mole of antibody are used in the process.

As a precautionary note, when the drug moiety of the derivatized drug has multiple reactive sites, it usually is necessary to block these sites with protecting groups. Certain aspects of the use of protecting group has been discussed supra, and others are well known to the ordinarily skilled organic chemist.

Products of this reaction are novel and are represented in formula I below

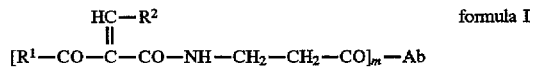

formula I wherein, $R^1$, $R^2$, m, and Ab are as defined above.

Finally, the immunoconjugate (drug-linker-antibody) is purified and isolated, usually by chromatographic methods. It may be possible to elute a conjugate from the chromatography medium in a concentration which is appropriate for administration to patients. Customarily, however, the immunoconjugate will be purified by chromatography and eluted with any convenient solvent, in the highest concentration which its solubility permits. A solvent solution containing 40% acetonitrile and 60% physiological phosphate buffered saline is preferred.

Compositions and Methods of Use

The immunoconjugates of the present invention are useful in the treatment methods of the present invention, particularly when parenterally administered in pharmaceutical compositions which are also an aspect of the present invention.

Such compositions, comprising an immunoconjugate of formula I and a parenterally-administrable medium, are formulated by methods commonly used in pharmaceutical chemistry. For example, the present immunoconjugates are acceptably soluble in physiologically acceptable fluids (carriers) such as physiological saline solutions, serum proteins such as human serum albumin, buffer substances such as phosphates, water, and electrolytes, and the like.

Products for parenteral administration are often formulated and distributed in a solid form preferably lyophilized, for reconstitution immediately before use. Such formulations are useful compositions of the present invention. Preparation of lyophilized compositions is well known in the art. Generally, such compositions comprise mixtures of inorganic salts which confer isotonicity, and dispensing agents, such as lactose, which allow the dried preparations to quickly dissolve upon reconstitution. Such formulations are reconstituted for use with highly purified water.

The most effective concentration of the immunoconjugates of the present invention in a composition of the present invention is dictated by the drug used in the conjugate, the physical properties of the drug and conjugate, and the final form of the composition. One skilled in the art of preparing such compositions will readily recognize the variables to be considered and the optimal ratio of composition components.

Similarly, the most effective dosage regimen for the immunoconjugate composition of the present invention depends upon the severity and course of the disease/infection, the patient's health and response to treatment, and the judgment of the treating physician. Accordingly, the dosages of the immunoconjugates and any accompanying compounds should be titrated to the individual treatment. Otherwise, guidance to the specific potencies of drugs and their appropriate dosage ranges is to be obtained from the standard medical literature.

The present invention also provides methods for treating susceptible mammalian cells or tissues comprising administering an effective amount of an immunoconjugate of formula I above to a mammal in need of such treatment.

Furthermore, the present invention provides a method of inhibiting the growth of pathogens in a mammalian host comprising administering an effective amount of an immunoconjugate of formula I above to a mammal in need of such treatment.

Alternative embodiments of the methods of this invention include the administration, either simultaneously or sequentially, of a number of different immunoconjugates bearing different drugs, or different antibodies or antigen-recognizing fragments thereof, for use in methods of combination chemotherapy.

For example, an embodiment of this invention may involve the use of a number of desacetylvinblastine-immunoconjugates where the specificity of the antibody component of the conjugate varies, e.g., a number of immunoconjugates are used, each one having an antibody that binds specifically to a different antigen or to different sites or epitopes on the same antigen present on the cell, tissue or pathogen of interest.

This embodiment may be especially useful in the treatment of certain tumors where the amounts of the various antigens on the surface of a tumor is unknown or the tumor cell population is heterogeneous in antigen expression and one desires to insure that a sufficient amount of drug is targeted to all of the cells at the tumor site. The use of a number of immunoconjugates bearing different antigenic or epitope specificities for the tumor increases the likelihood of obtaining sufficient drug at the tumor site. Additionally, this embodiment is important for achieving a high degree of specificity for the tumor because it is known in the art that the likelihood that normal tissue will possess all of the same tumor-associated antigens is small [see, for example, Hellstrom, I., et al., *J. Immunol.*, 127, 1: 157–160 (1989)].

Alternatively, a number of different immunoconjugates can be used where only the drug component of the conjugate varies. For example, a particular antibody can be linked to doxorubicin to form one immunoconjugate and can be linked to lometrexol to form a second immunoconjugate. Both conjugates can then be administered to a host to be treated and will localize, because of the antibody specificity, at the site of the selected target cell, tissue or pathogen to be treated. This embodiment may be important when administering an immunoconjugate to a cell, tissue or host bearing a pathogen to be treated where the target is known or suspected to be resistant to a particular drug or class of drugs.

In order that the invention described herein may be more fully understood, the following examples are set forth. It should be understood, however, that these examples are only for illustrative purposes and are not to be construed as s limiting the scope of this invention in any manner.

EXAMPLE 1

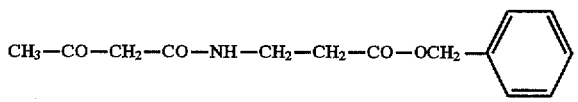

To a round bottom flask equipped with a stirrer, drying tube and therometer, containing 50 mL of dichloromethane and 10 mL of dry dimethyformamide (DMF), 3.8 grams of β-alanine benzyl ester HCl was added. When solution had been obtained, 1.9 gm of N-methylmorpholine was added and the mixture was cooled to less than 4° C. Next, 1.9 grams of diketene was dissolved in 25 mL of dichloromethane and the resulting solution was added dropwise to the flask at a rate which allowed the temperature to be maintained at less than 5° C. Following the addition of diketene, the reaction was stirred for 15 minutes, warmed to room temperature and again stirred for 1.5 hours. The reaction mixture was concentrated in vacuo over night and gave an orange viscous residue which was dissolved in ethyl acetate brine. The ethyl acetate layer was separated and sequentially washed with 10% citric acid solution, brine, saturated sodium carbonate, and brine. The resulting ethyl acetate solution was dried over magnesium sulfate and concentrated in vacuo to a pale orange liquid which was solidified upon standing at room temperature to give 4.18 grams (91%) of orange solid. NMR was used to confirm the identity of the title compound.

EXAMPLE 2

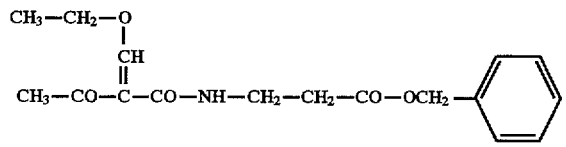

To a round bottom flask equipped with a stirrer, drying tube and thermometer, containing 4.7 mL of acetic anhydride and 3.3 mL of triethylorthoformate, 2.0 grams of the product from Example 1 was added and the solution was heated to reflux for 2 hours. Excess acetic anhydride and triethylorthoformate were removed in vacuo and a dark red viscous liquid remained. The red viscous liquid was dissolved in a minimum volume of ethyl acetate, and hexane was added to cloudiness. This mixture was poured into a 150 mL fritted glass Buchner funnel which was 75% full with silica gel 60. The gel was eluted with 500 mL of 20% ethyl acetate in hexane, 500 mL of 30% ethyl acetate in hexane, and 500 mL of 40% ethyl acetate in hexane, and each fraction was collected. The last two fractions were combined and concentrated in vacuo to give 1.23 grams (51%) of pale yellow syrup. The identify of the title compound was confirmed by NMR.

EXAMPLE 3

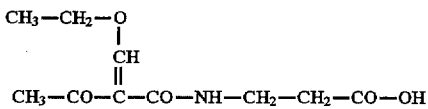

Into a 50 mL round bottom flask equipped with a magnetic stirrer, was suspended 5% palladium-on-carbon catalyst (Pd/C) in 10 mL of absolute ethanol. To this was added 1.2 grams of the reaction product from Example 2 in 10 mL of absolute ethanol, followed by the addition of 0.7 mL of 1,4-cyclohexadiene. After stirring the mixture for 30 minutes at room temperature, the mixture was heated to 65° C. for 30 minutes. After the Pd/C was removed by filtration, the residue was eluted with hot ethyl acetate to give 0.28 grams (32%) of off-white crystals by filtration. NMR was used to confirm the identity of the title compound.

EXAMPLE 4

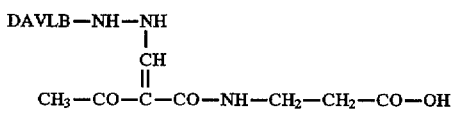

To a 10 mL round bottom flask equipped with a magnetic stirrer and containing 0.8 mL of dry DMF, 278.0 mg of desacetylvinblastine-hydrazide.$H_2SO_4$ (DAVLB-hydrazide-$H_2SO_4$) was added and dissolved. To this solution was added 73.5 mg of the reaction product from Example 3 and also dissolved. The reaction was monitored by HPLC (Waters Radial pak $C_{18}$, flow rate of 5 mL/minute, using 65% MeOH:35% 0.1M pH=7.0 $KH_2PO_4$). HPLC showed that the title conjugate was formed within 20 minutes.

EXAMPLE 5

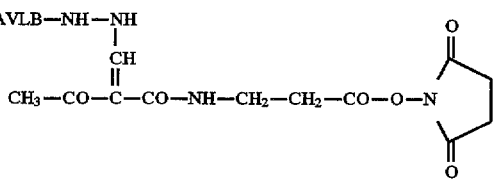

The reaction flask from Example 4 was fitted with a septum and drying tube and cooled to less than −20° C. To the reaction flask which contained the solution from Example 4 was added 300 μL of a solution of 91 mg of N-hydroxy-succinimide in 369.0 μL of dry DMF. The solution was stirred for 10 minutes at −20° C and then allowed to gradually warm to room temperature. The solution was continuously stirred overnight. The following day, the DMF was removed in vacuo with heat, (less than 65° C.), and the resulting viscous orange liquid was sealed and stored at less than −4° C. for at least two days. Following removal from storage, the excess N-hydroxy-succinimide crystals were selectively removed by dissolving the viscous orange liquid in dichloromethane and filtering. The product remaining in solution was precipitated by the addition of ether, redissolved in dichloromethane and reprecipitated with ether three times. Following centrifugation, the residue was redissolved in dichloromethane, transferred to a round bottom flask and concentrated in vacuo to give 370 mg of off-white solid. A small portion of the solid was dissolved in DMF, treated with isopropylamine and analyzed by HPLC which showed clean conversion to the title product.

EXAMPLE 6

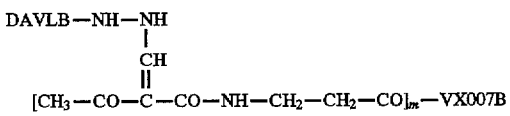

Antibody VX007B is produced by a hybridoma which is a subclone derived from the hybridoma producing the antibody KS1/4, which is discussed above in the antibody section of this document. A 500.0 μL portion of a solution containing 9.9 mg (19.8 mg/mL) of that antibody in 0.34M sodium borate was added to a 3.0 mL vial equipped with a magnetic stirrer. To this solution was added 40.5 μL of a mixture of 2.4 mg of the product from Example 5 in 177 μL of dry DMF to deliver 0.55 mg of the product from Example 5. This solution was stirred at room temperature for 20 minutes and centrifuged for 5 minutes. A 1.0 mL portion of the supernatant was applied to a phenylsuperose column [FPLC, HR 5/5 (Pharmacia, Inc., Piscataway, N.J.)] equilibrated with 0.1M physiological phosphate buffered saline (ppbs), and eluted via a step gradient with a solution containing 40% acetonitrile and 60% 0.1M ppbs. Three pooled fractions were collected. A 500 μL portion of each of the 3 pools was purified on superose 12 (elution with 10% acetonitrile in ppbs) and analyzed by ultraviolet (UV) spectrophotometry. UV analysis indicated a total recovery of 4.4 mg of conjugate (45%). The conjugation ratio for the three pools was 3.3, 4.5, and 6.3 moles of drug (m) per mole of antibody, respectively.

EXAMPLE 6A

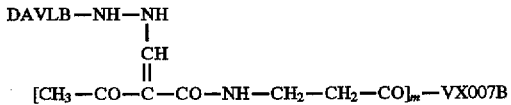

The process of Example 6 was followed, starting with 9.9 mg of antibody and 0.69 mg of the product from Example 5. The total recovered immunoconjugate amounted to 3.0 mg (30%) and the conjugation ratio for the three pools were 4.1, 4.5 and 7.2 moles of drug (m) per mole of antibody, respectively.

EXAMPLE 7

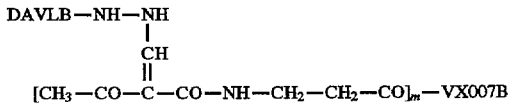

A 1.0 mL portion of a solution containing 18.9 mg of antibody VX007B in 0.1M phosphate buffer was added to a 3.0 mL vial equipped with a magnetic stirrer. To this solution was slowly added a mixture of 1.59 mg of the product from Example 5 in 81.1 μL of dry DMF. This solution was stirred for two hours at room temperature and centrifuged for 10 minutes. The supernatant was injected into a phenyl superose column as described in Example 6 which was equilibrated with 0.1M ppbs, and eluted via a step gradient with a solution containing 40% acetonitrile in 0.1M ppbs. One pooled fraction was collected. The fraction was filtered through a Millex-GV® (Millipore, Bedford, Mass.) 0.22μ filter and submitted for UV analysis which indicated a total recovery of 10.4 mg (55%) and a conjugation ratio of 4.0 moles of drug (m) per mole of antibody.

EXAMPLE 7A

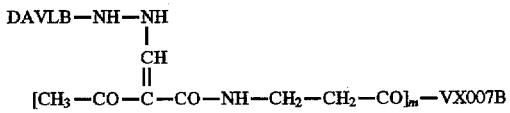

The process of Example 7 was followed, except the phenylsuperose column was equilibrated with 0.1M acetate buffer, and eluted with a solution containing 40% acetonitrile in 0.1M acetate buffer. Of the single pooled fraction, 2 mL was injected into a Sephadex G-25 M® column (Pharmacia) and the collected pool fractions were submitted for UV analysis. The UV analysis indicated a total recovery of 7.9 mg (42%) and the ratio was 4.4 moles of drug (m) per mole of antibody.

EXAMPLE 8

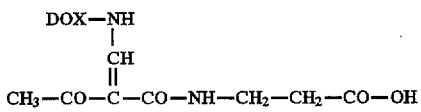

To a 10 mL round bottom flask equipped with a magnetic stirrer and supplied with a nitrogen atmosphere, and containing 4 mL of DMF, was suspended 200.0 mg of doxorubicin. To this suspension was added 0.75 mL of saturated sodium bicarbonate solution which gave a dark red homogeneous solution. Next, 95 mg of the produce from Example 3 were added and the solution was allowed to stand at room temperature. The reaction was monitored by HPLC [Waters C18 Radial pak column, flow rate of 5 mL/minute, using 65% MeOH:35% NaOAc solution (3%w/v)] and, after three hours, the title compound was identified. After storing the reaction mixture overnight at 4° C., the reaction mixture was allowed to warm to room temperature, added to 50 mL of water and twice washed with 150 mL of ethanol. The resulting solution was then acidified to a pH of 3.0 with 0.2N HCl and quickly extracted into two portions each of 150 mL of ethanol. The ethanol extracts were pooled dried over magnesium sulfate and concentrated in vacuo to give 242.8 (97%) of dark red solid. HPLC analysis of this material confirmed the identity of the title derivatized drug.

EXAMPLE 9

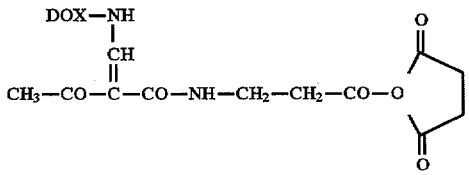

To a 10 mL round bottom flask equipped with a magnetic stirrer supplied with a dry nitrogen atmosphere, and containing 4 mL of DMF, was added 194.4 mg of the Doxorubicin derivative from Example 8. To this solution were added 256.4 mg of 1-ethyl-3-(3-dimethyl-aminopropyl) carbodiimide.HCl and, 15 minutes later, 153.94 mg of N-hydroxysuccinimide. The reaction was monitored by HPLC (Waters $C_{18}$ radial pak column as previously-described). Three hours after the addition of the last reactant, the reaction was complete and the title derivatized drug was identified. Although the reaction mixture was stirred overnight at room temperature under a nitrogen atmosphere, it is best to work up the reaction mixture after three hours.

For work up, the entire reaction mixture was extracted into ethyl acetate with sodium chloride solution and twice washed with the sodium chloride solution and once with water. The resultant mixture was dried over magnesium sulfate, filtered and concentrated in vacuo to give about 250 mg of red residue. The residue was dissolved in 20 mL of dichloromethylene and 50 mL of ethanol was added. The precipitate of product which immediately formed was filtered and dried to give 174.2 mg (79%) of red powder. HPLC analysis of this powder confirmed the identity of the title derivatized drug.

EXAMPLE 10

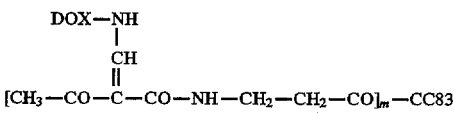

A 741.0 µL portion of a solution containing 10.0 mg (13.5 mg/mL) of antibody CC83 (as discussed supra) in 0.1M physiological phosphate buffered saline (ppbs) was added to a 3 mL round bottom flask equipped with a magnetic stirrer. To this solution were added 60.1 µL of a mixture of 1.5 mg of the product from Example 9 in 164.0 µL of dry DMF to deliver 0.55 mg of the product from Example 9. The reaction mixture was slowly stirred for 1.5 hours at room temperature, transferred to a centrifuge tube and centrifuged for 10 minutes. The supernatant was injected into a phenyl-superose column (FPLC; HR 5/5) equilibrated with a solution which contained 62.5% 0.1M of ppbs and 37.5% of a buffer containing 40% acetonitrile and 60% 0.1M ppbs. Three pooled fractions were collected. The second and third fractions were pooled and a 2.0 mL portion of this pool was injected into a Sephadex G-25 column (HR 16/50) equilibrated and eluted with 0.1M ppbs. The column was eluted, via a step gradient, with the solution containing 40% acetonitrile and 60% 0.1M ppbs. The pooled fractions gave about 8.0 mL of orange solution which was filtered through a Millex-GV® 0.22µ filter and analyzed by UV. The UV analysis indicated a total recovery of 7.8 mg of conjugate (78%), and the conjugation ratio was 3.9 moles of drug (m) per mole of antibody.

EXAMPLE 10A

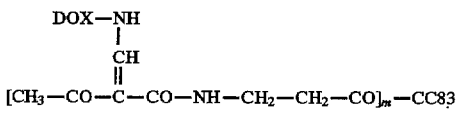

The process of Example 10 was followed except for the buffer in which the antibody solution was prepared and the length of time the reaction mixture was stirred prior to centrifugation. Rather than using 0.1M ppbs, 0.34M borate buffer was employed. Also, the reaction mixture was stirred for 20 minutes rather than 1.5 hours. UV analysis indicated a total recovery of 8.7 mg of conjugate (87%), and the conjugation ratio was 5.2 moles of drug (m) per mole of antibody.

EXAMPLE 11

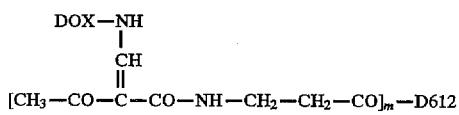

Antibody D612 is produced by a 658.0 µL portion of a solution containing 10 mg (15.2 mg/mL) of antibody D612 in 0.1M ppbs was added to a 3 mL round bottom flask. To this solution were added 53.3 µL of a mixture of 2.10 mg of the product from Example 9 in 204.0 µL of dry DMF to deliver 0.55 mg of the product from Example 9. The reaction mixture was slowly stirred for 20 minutes at room temperature, transferred to a centrifuge tube and centrifuged for 10 minutes. The supernatant was injected into a phenyl-superose column (FPLC; HR 5/5) equilibrated with a solution which contained 62.5% of 0.1M ppbs and 37.5% of a buffer containing 40% acetonitrile and 60% of 0.1M ppbs. The column was eluted, via a step gradient, with the solution containing 40% acetonitrile and 60% of 0.M ppbs. Three pooled fractions were collected. The second and third fractions were pooled and a 2.0 mL portion of this pool was injected into a Sephadex G-25 M column (HR 16/50) equilibrated with 0.1M ppbs. The pooled fractions gave about 8.0 mL of orange solution which was filtered through a Millex-GV 0.22µ filter and analyzed by UV. The UV analysis indicated a total recovery of 7.6 mg of conjugate (76%), and the conjugation ratio was 4.1 moles of drug (m) per mole of antibody.

EXAMPLE 11A

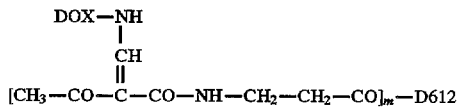

The process of Example 11 was followed except for the buffer in which the antibody solution was prepared. Rather than using 0.1M ppbs, 0.34M borate buffer was employed. UV analysis indicated a total recovery of 6.1 mg of conjugate (61%), and the conjugation ratio was 6.1 moles of drug (m) per mole of antibody.

Test I

UCLA/P3 Tumors in Mice

The conjugate of Example 6 was tested in vivo against xenografts of the UCLA/P3 lung adenocarcinoma in female Charles River nude mice. The test was begun by subcutaneously implanting each mouse with $10^7$ UCLA/P3 tumor cells. On each of days 2, 5 and 7 after implantation, each mouse was injected with the conjugate or with the unconjugated drug as a comparative base. The conjugate was the product of Example 6 and the drug was desacetylvinblastine-hydrazide.$H_2SO_4$. The doses of drug alone, or as a component of the conjugate ranged from 0.5 to 3.0 mg/kg. The size of the tumor induced by implantation was measured, if possible, 14, 21 and 28 days after implantation and the percent inhibition was calculated. Each treatment group consisted of 5 mice.

The following table reports the activity of the drug and the conjugate as % inhibition of the tumors.

| Days After | % Inhibition of the Tumor | | |
|---|---|---|---|
| Implantation | Drug | Drug Dosage | Conjugate |
| 14 | 92* | 3.0 mg/kg | 100** |
| 21 | 89 | | 100 |
| 28 | 69 | | 100 |
| 14 | 80 | 1.0 mg/kg | 100 |
| 21 | 71 | | 100 |
| 28 | 64 | | 100 |
| 14 | 79 | 0.5 mg/kg | 100 |
| 21 | 50 | | 100 |
| 28 | 48 | | 100 |

*Mouse mortality 1/5
**Mouse mortality 2/5

Test II

UCLA/P3 Tumors in Mice

The procedure from Test I was used to establish UCLA/P3 lung adenocarcinoma in female Charles River nude mice. On each of days 2, 5 and 7 after implantation, each mouse was injected with the conjugate (VX007B-F(ab')2-desacetylvinblastine adduct from Example 5), desacetylvinblastine-hydrazide-$H_2SO_4$ alone, or the i.v. excipient alone. To dosage of drug, either alone or as a component of the conjugate, range from 0.25 to 1.0 mg/kg.

The following table reports the activity of the conjugate, drug and control as mean tumor mass (mg) of existing tumors measured 24 days following implantation.

| Drug Dosage | Mean Tumor Mass, mg | | |
|---|---|---|---|
| mg/kg | Conjugate | Drug | Control |
| 2.0 | 0 | 50 | 520 |
| 1.0 | 20 | 140 | 510 |
| 0.50 | 50 | 505 | 505 |
| 0.25 | 305 | 620 | 505 |

We claim:

1. A compound of the formula

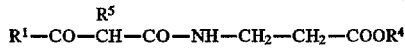
$$R^1-CO-CH-CO-NH-CH_2-CH_2-COOR^4$$
with $R^5$ above CH wherein $R^1$ is $C_1$-$C_4$ alkyl;

$R^4$ is a carboxy protecting group;

$R^5$ is H =C(OH)2, =CHR$^6$, or =CHSR$^6$; and $R^6$ is $C_1$-$C_4$ alkyl.

2. The compound of claim 1 wherein $R^1$ is methyl and $R^5$ is H.

3. The compound of claim 2 wherein $R^4$ is benzyl.

4. The compound of claim 1 wherein $R^1$ is methyl, $R^5$ is =CHR$^6$, and $R^6$ is ethyl.

5. The compound of claim 4 wherein $R^4$ is benzyl.

6. A compound of the formula

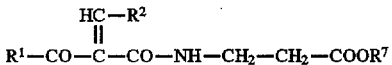
$$R^1-CO-C-CO-NH-CH_2-CH_2-COOR^7$$
with HC-$R^2$ above C wherein $R^1$ is $C_1$-$C_4$ alkyl;

$R^2$ is a monovalent drug derivative having a reactively-available amino, hydroxy or thiol function to which the =CH— is attached; and $R^7$ is H, a carboxy protecting group, or a carboxy activating group, or a moiety which completes a salt of the carboxy group.

7. The compound of claim 6 wherein $R^2$ is the residue of a drug which has a cytotoxic effect on susceptible cancer cells.

8. The compound of claim 7 wherein $R^1$ is methyl and $R^2$ is desacetylvinblastine or a derivative thereof.

9. The compound of claim 1 wherein $R^7$ is H.

10. The compound of claim 8 wherein $R^7$ is a carboxy protecting group.

11. The compound of claim 10 wherein $R^7$ is benzyl.

12. The compound of claim 7 wherein $R^7$ is a carboxy activating group.

13. The compound of claim 12 wherein $R^7$ is succinimidyl.

14. The compound of claim 12 wherein $R^1$ is methyl and $R^2$ is doxorubicin or a derivative thereof.

15. The compound of clam 14 wherein $R^7$ is H.

16. The compound of claim 14 wherein $R^7$ is a carboxy protecting group.

17. The compound of claim 16 wherein $R^7$ is benzyl.

18. The compound of claim 14 wherein $R^7$ is a carboxy activating group.

19. The compound of claim 18 wherein $R^7$ is a succinimidyl.

* * * * *